United States Patent [19]

Goldstein et al.

[11] Patent Number: 4,963,431
[45] Date of Patent: Oct. 16, 1990

[54] ZEOLITE-IMPREGNATED PADS

[75] Inventors: Joel M. Goldstein, Ambler, Pa.; Thomas M. O'Malley, Uxbridge, Mass.

[73] Assignee: Aquarium Pharmaceuticals, Inc., Chalfont, Pa.

[21] Appl. No.: 208,316

[22] Filed: Jun. 17, 1988

[51] Int. Cl.$^5$ .............................................. D04H 1/58
[52] U.S. Cl. .................................. 428/288; 428/219; 428/290; 428/297; 428/360
[58] Field of Search ............... 428/283, 288, 290, 297, 428/360, 361, 402, 407, 219

[56] References Cited

U.S. PATENT DOCUMENTS

| | | | |
|---|---|---|---|
| 2,988,441 | 6/1961 | Pruitt | 71/27 |
| 3,562,952 | 2/1971 | Bramante | 47/34 |
| 3,608,238 | 9/1971 | Reuter | 47/34 |
| 3,776,188 | 12/1973 | Komakine | 424/76 |
| 3,866,352 | 2/1975 | Herveling et al. | 47/34 |
| 3,898,324 | 8/1975 | Komakine | 424/76 |
| 3,961,445 | 6/1976 | Rack | 47/37 |
| 3,973,355 | 8/1976 | McKenzie | 47/37 |
| 4,004,369 | 1/1977 | Kato et al. | 47/62 |
| 4,059,543 | 11/1977 | Koovsky et al. | 55/75 |
| 4,074,997 | 2/1978 | Cohen | 71/24 |
| 4,114,316 | 9/1978 | Cohen | 47/64 |
| 4,160,059 | 7/1979 | Samejima | 428/288 |
| 4,256,728 | 3/1981 | Nishino et al. | 422/4 |
| 4,305,782 | 12/1981 | Ostreicher et al. | 162/181 C |
| 4,343,109 | 8/1982 | Holtkamp | 47/81 |
| 4,395,332 | 7/1983 | Klein | 210/496 |
| 4,437,429 | 3/1984 | Goldstein et al. | 119/1 |
| 4,488,969 | 12/1984 | Hou | 210/679 |
| 4,525,410 | 6/1985 | Hagiwara et al. | 428/296 |
| 4,565,727 | 1/1986 | Giglia et al. | 428/172 |
| 4,793,837 | 12/1988 | Pontius | 428/281 |

Primary Examiner—James J. Bell
Attorney, Agent, or Firm—Panitch Schwarze Jacobs & Nadel

[57]  ABSTRACT

Zeolite-impregnated pads useful for filtering and removing ammonia from fluids and for enhancing plant growth and microbial activity comprise a nonwoven polymer pad having zeolite bonded substantially throughout the pad by a non-toxic adhesive composition. In addition, methods for removing ammonia from fluids comprise passing fluid through zeolite-impregnated pads, and methods for growing plants in situ and methods for growing bacteria comprise using zeolite-impregnated pads to enhance growth.

22 Claims, 2 Drawing Sheets

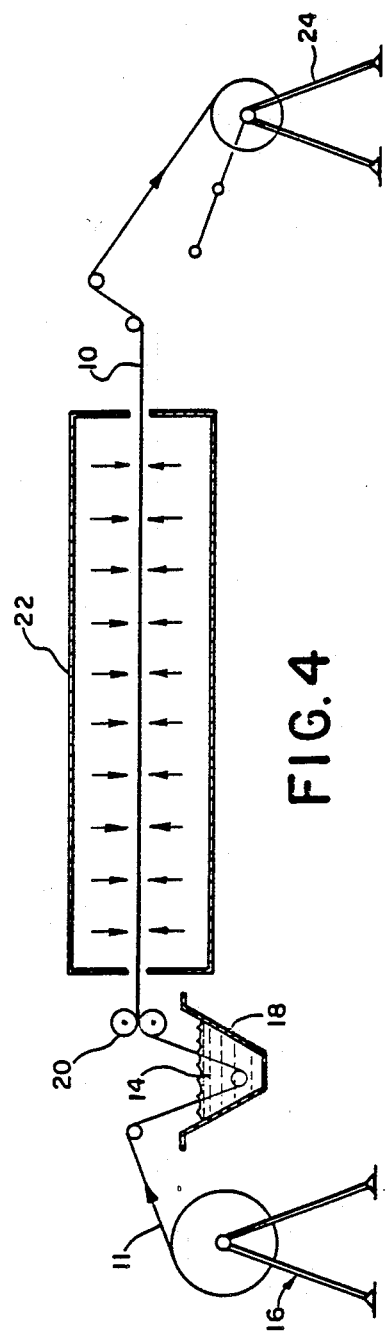

ZEOLITE-IMPREGNATED PADS

BACKGROUND OF THE INVENTION

1. Field Of The Invention

The present invention relates to zeolite-impregnated nonwoven polymer pads useful for filtering and removing ammonia from fluids and for enhancing plant growth and microbial activity, and methods of producing such zeolite-impregnated pads. In addition, the present invention is directed to methods for removing ammonia from fluids, methods for growing plants in situ and methods for growing bacteria using the zeolite-impregnated pads.

2. Description of the Prior Art

It is known in the biological arts that a significant function of animal metabolism is to eliminate or excrete ammonia and other toxins from the body. However, when toxins are eliminated into or are already present in a relatively enclosed environment, such as enclosed air spaces and finite areas of water or land, such as aquariums, fish ponds, cages, carrying cases and other relatively confined animal habitats, toxins may readily be reingested. Toxins and other waste products may accumulate and become odiferous and offensive. In fish aquariums, for example, ammonia is a pervasive and persistent toxin causing fish illness and death. Ammonia is continually being produced in the aquarium environment by decaying food, decaying solid waste matter, fish respiration and fish urine. Ammonia accumulates in a typical aquarium environment and becomes increasingly dangerous to fish health. Conventional methods for removing or neutralizing ammonia include the use of zeolite in the form of loose chips in an aquarium filter container through which aquarium water must pass as the water is being filtered. Such methods, however, are generally inconvenient and inefficient because the proper amount of zeolite chips must be measured and added to the aquarium filter container. The zeolite chips are also difficult to remove and replace.

Other methods are somewhat objectionable in that they require the addition of chemicals which are costly and potentially dangerous to aquarium animals and plants.

Waste elimination from animals is another example where ammonia and similar nitrogenous compounds generally result in noxious odors, in particular ammonia odor. Such odors are particularly acute in enclosed areas, such as buildings and homes. Conventional methods to deodorize or filter odors form air include U.S. Pat. Nos. 3,776,188 and 3,898,324 concerning inhibiting the formation of odors from poultry farms. These patents disclose the use of a dried fine powder of zeolite mixed with a coarse powder of crystalline ferrous sulfate hepta-hydrate. The use of zeolites in these patents is to impart stability, while the deodorizing is accomplished by the sulfate hepta-hydrate.

In U.S. Pat. No. 4,256,728, zeolites are used as support for an acid, such acid serving as the deodorization agent.

U.S. Pat. No. 4,059,543 discloses the use of clinoptilolite, a zeolite, in the ammonia exchanged form and treated with a dilute solution of a strong acid to act as an absorbent for acid gases.

Zeolites are known to possess excellent adsorption capacity for nitrogen as contained in ammonia and other nitrogenous chemicals as well as positively charged minerals, including calcium, iron, magnesium and copper, among others. The zeolite absorption mechanism is an ion exchange system whereby ammonium ions and other ions having similar positive charges are ionically bonded to the zeolite surface. Where zeolite is ground into a fine powder form, there is a high surface area of zeolite to which ammonia and other compounds and minerals may become adsorbed. However, zeolite powders are difficult to use efficiently without some form of containment that does not adversely affect zeolite activity and does not overly compromise the advantageous high zeolite surface area.

U.S. Pat. No. 4,437,429 discloses the use of hydrated zeolite for controlling odors emanating from pet litter, such as cat litter. This patent discloses the use of a pad of sorptive sheet material filled with zeolite. The adsorptive and other chemical properties of zeolites in general are also disclosed by this patent. Nothing in this patent, however, discloses the use of zeolite in environments other than animal litter, such as aquatic and land environments.

Nitrogenous chemicals are known nutrient sources or fertilizers for plants and nitrifying bacteria. Fertilizers, such as urea, are generally available as granulated powders or liquids which may be added to plant habitats to enhance plant growth. However, such fertilizers are generally inconvenient and inefficient because the proper amount of fertilizer must be added and may, especially in aquatic environments, cause cloudiness of the water and may harm animal life present therein.

Bio-Chem Beads TM biological filter material, available from Aquarium Pharmaceuticals, Inc., provides a physical habitat for nitrifying bacteria in microporous beads. Such beads, however, have no chemical attraction for ammonia and other nitrogenous compounds and do not, therefore, supply a nutrient source for nitrifying bacteria or a medium where such nutrients may be concentrated.

In view of the deficiencies and inefficiencies of the prior art, it would be desirable to have a zeolite-containing pad which may be used to remove or neutralize ammonia and other chemicals and minerals from fluid and land environments and/or used to enhance plant and microbial growth, which is relatively simple to produce, easy to use and effective.

SUMMARY OF THE INVENTION

According to the present invention, a zeolite-impregnated pad comprises a permeable, nonwoven polymer pad having zeolite bonded throughout the pad by a non-toxic adhesive composition in an amount sufficient to securely bind the zeolite to the nonwoven polymer pad without adversely affecting zeolite activity.

Further, the present invention is directed to a method for manufacturing zeolite-impregnated pads, wherein the zeolite is securely bonded substantially throughout the pad without zeolite activity being adversely affected, comprising the steps of providing a permeable, nonwoven polymer pad, impregnating the polymer pad with a non-toxic zeolite-adhesive slurry, which is prepared by mixing a liquid vehicle and zeolite, adding and mixing binder, and curing the impregnated pad to bind the zeolite substantially throughout the pad.

In addition, the present invention is directed to a method for removing ammonia from an ammonia containing fluid comprising passing the fluid through a porous filter comprising a zeolite-impregnated pad.

The present invention is also directed to a method for growing a plant in situ comprising placing a zeolite-impregnated pad having nitrogen adsorbed thereby adjacent to roots of the plant so that the roots receive the nitrogen.

In addition, according to the present invention a method for growing bacteria comprises contacting a zeolite-impregnated pad with bacteria in the presence of nitrogen.

BRIEF DESCRIPTION OF THE DRAWINGS

The foregoing summary of the invention, as well as the following detailed description of preferred embodiments, will be better understood when read in conjunction with the appended drawings. For the purpose of illustrating the invention, there is shown in the drawings an embodiment which is presently preferred, it being understood, however, that the invention is not limited to the specific arrangements and instrumentalities disclosed. In the drawings:

FIG. 4 is a schematic diagram illustrating a method for producing zeolite-impregnated pads.

DETAILED DESCRIPTION OF PREFERRED EMBODIMENTS

Figure 1:
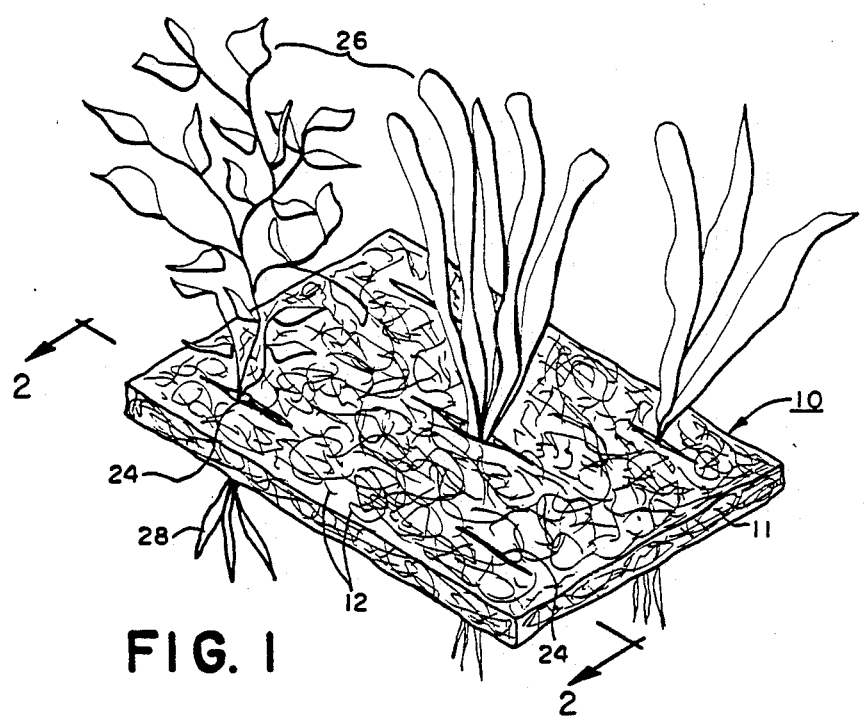
FIG. 1 is a generalized isometric view showing a zeolite-impregnated, lofty, nonwoven pad having slits therethrough as the pad might be used for growing plants.
Figure 2:
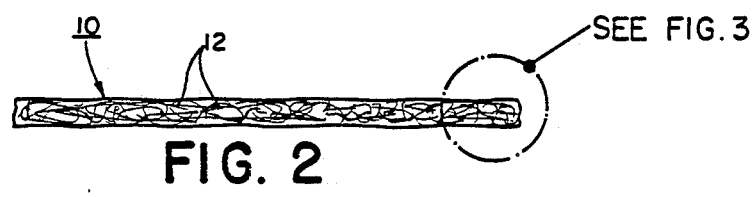
FIG. 2 is a cross-sectional view of the pad along line 2—2 in FIG. 1.
Figure 3:
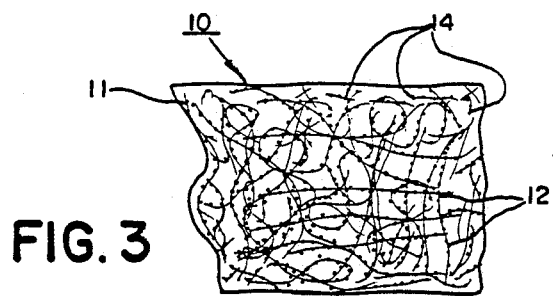
FIG. 3 is an enlarged view of the cross-sectional view in FIG. 2 showing a representative drawing of zeolite particles bonded to the pad fibers according to the present invention.

Referring to the drawings, wherein the numerals indicate like elements throughout the several views, there is shown in FIGS. 1, 2 and 3 a zeolite-impregnated pad 10 according to the present invention.

In accordance with the present invention, the substrate for the zeolite-impregnated pad 10 comprises a nonwoven polymer pad 11. More preferably, the nonwoven pad 11 comprises a lofty, nonwoven mat or pad of polymeric fibers 12 generally randomly oriented throughout the pad 11 and bonded together at points where the fibers 12 contact each other. The fibers 12 may be of any length suitable for forming nonwoven pads 11 and should be strong enough to withstand pad processing (discussed below) in accordance with the present invention. Generally, fibers having a tensile strength greater than about 4 g/denier are sufficiently strong enough to withstand pad processing methods in accordance with the present invention. Generally also, fibers having varying lengths may be used to produce a nonwoven polymer pad. Typically, fibers about 2 inches to about 4 inches in length are used in accordance with the present invention although one skilled in the art will appreciate that longer and shorter fibers may be used.

Preferably, the pad fibers 12 are bonded together at points where the fibers contact each other by an acrylic binder or a polymer resin. It is presently preferred that polyvinyl chloride (PVC) is used to bond the fibers 12 in accordance with the present invention. One skilled in the art will recognize that such polymeric fibrous pads are generally known and may be formed, for example, on a Rando-Webber machine from natural or synthetic polymeric fibers 12. Examples of synthetic polymeric fibers include polyester, polypropylene, rayon and nylon. Preferably, the fibers 12 comprise polyester and, more preferably, polyethylene terephthalate polyester. Manufacturers of such nonwoven polyester pads include the Union Wadding Company in Pawtucket, R.I., Cumulus Fibers, Inc. in Charlotte, N.C. and Moldan, Inc. in North Carolina.

Fibers 12 of about 5 denier to about 25 denier may be used in accordance with the present invention. It has been found in accordance with the present invention that while a pad 11 having uniform single denier fibers 12 is suitable, a pad having mixed denier fibers 12 provides surprisingly superior results. For example, in one embodiment of the present invention, a lofty, nonwoven polyester pad 11 made on a Rando-Webber machine comprises fibers 12 of about 6, 15 and 25 denier, where more than about two thirds of the fibers comprising the pad are about 15 denier. In this embodiment, fibers 12 of about 6 denier comprise about 15% to about 20% of the polyester fiber pad 11; fibers of about 15 denier comprises about 60% to about 70% of the polyester fiber pad; and fibers of about 25 denier comprise about 15% to about 20% of the polyester fiber pad.

In another embodiment of the present invention, the polyester pad 11 comprises fibers of about 6, 8 and 25 denier, present in an amount about one third each of the total fibers of the pad.

One skilled in the art will appreciate, however, that other, larger and smaller denier fibers 12 in greater and less concentrations may be used to form a lofty, nonwoven polymer pad 11 in accordance with the present invention.

Where the polymer pad 11 comprises nonwoven polyester fibers, it is presently preferred that the pad has a thickness of about 0.125 inch to about 2.0 inches or more, depending on the limitations of the equipment used to manufacture the zeolite-impregnated pads. Generally, pads having a thickness greater than about 2 inches are difficult to manipulate in machines currently available for saturating and drying (discussed below) zeolite-impregnated pads in accordance with the present invention.

The particular thickness of the pad is based on the particular use desired. Moreover, it is preferred that such a pad has a weight of about 2 oz/yd$^2$ to about 13 oz/yd$^2$, also depending on the particular use desired. For example, where it is desired to use the zeolite-impregnated pad in a liquid environment, such as for use in an aquarium as an ammonia adsorbing filter, the pad may have a thickness of about 0.50 inch having a weight of about 9 oz/yd$^2$. Where it is desired, for another example, to use the zeolite-impregnated pad 10 in a gaseous environment, such as air, the pad may have a thickness of about 0.25 inch having a weight of about 4 oz/yd$^2$. The type and amount of chemicals to be adsorbed by the zeolite may also help to determine the thickness and weight of a pad 11 used in accordance with the present invention. One skilled in the art may easily determine the desired thickness of a zeolite-impregnated pad in accordance with the present invention based on desired use.

Further according to the present invention, zeolite is bonded substantially throughout the pad 10. Zeolites are a group of aluminosilicates having a tetrahedral framework and are generally used as a very fine powder. Several examples of zeolites, their general characteristics and geographic points of mining zeolites are disclosed in U.S. Pat. No. 4,437,429. The disclosure of this patent is incorporated herein by reference. Zeolite is a commonly available mineral having the general formula $MO.Al_2O_3.nSiO_2.xH_2O$, wherein M is Na, K, Ca, Sr, or Ba, and n and x are integers. Such zeolites commonly occur as late minerals in amygdaliodal basalts, as devitrification products, as authigenic minerals in sandstones and other sediments, and as alteration products of feldspars and nepheline.

Various zeolites may be mined in a variety of areas throughout the world in various forms generally described in U.S. Pat. No. 4,437,429. As used herein, the word "zeolite" refers to uncalcined, hydrated zeolite. The zeolite is not heat-treated (calcined) and thus it contains its original water of hydration. It is not sufficient that water is added to a previously heat-treated zeolite in which the original water of hydration was driven-off.

Preferably, the zeolite used in the present invention is selected from the group consisting of analcime, sodalite, chabazite, natrolite, phillipsite, mordenite and clinoptilolite. The presently preferred zeolite comprises clinoptilolite.

It is presently preferred that the zeolite is a powdered zeolite, each particle or grain being about 1 micron to about 100 microns in size. More preferably, the zeolite grains are up to about 44 microns in size. More preferably still, the zeolite grains are about 3 microns to about 12 microns in size. Generally, as the zeolite grain size decreases (or the finer the zeolite powder), the more zeolite surface area becomes available for adsorption. In addition, as the zeolite grain size increases, the zeolite particles tend to become more difficult to suspend in the adhesive composition (discussed below) and more difficult to use in manufacturing zeolite-impregnated pads in accordance with the present invention. One skilled in the art will understand, however, that finer and coarser zeolite powders may be used in accordance with the present invention.

In accordance with the present invention, zeolite in the form of small particles or a powder is bonded substantially throughout the nonwoven polymer pad 11 by a non-toxic adhesive composition. The zeolite and adhesive composition are combined to form a zeolite-adhesive slurry 14. Preferably, the slurry 14 is an emulsion or suspension. The non-toxic adhesive composition used in the zeolite-adhesive slurry (discussed below) comprises a liquid vehicle and a binder component. More preferably, the adhesive composition comprises a liquid vehicle which is most typically water, a binder component, a polymeric thickener and an anti-foaming agent. These components of the adhesive composition should not be toxic or offensive to plants and animals which may directly or indirectly contact the impregnated pad or its component parts and should not adversely affect zeolite activity by, for example, adhering to or coating a major portion of the active surface of the zeolite.

It is presently believed that the components of the adhesive composition may be present in percent by weight amounts of the adhesive composition as follows: liquid vehicle, about 63% to about 93%; binder, about 14% to about 21%; thickener, where desired, about 3% to about 6%; and an anti-foaming agent, where desired, less than about 1%. It is presently preferred that the liquid vehicle comprises about 78% by weight of the adhesive composition; the binder comprises about 17%; the thickener comprises from about 4 to about 5%; and the anti-foaming agent comprises less than about 1%.

It is preferred that the liquid vehicle comprises water. One skilled in the art will recognize that water is non-toxic and is generally the easiest, safest and most economical liquid vehicle used for polymer suspensions. It will be appreciated by one skilled in the art, however, that other suitable liquid vehicles may be used in accordance with the present invention. The liquid vehicle is preferably present in an amount suitable to suspend the remaining components in the adhesive composition. Where it is desired to have a more viscous adhesive composition, less liquid vehicle may be used. One skilled in the art may readily determine the amount of liquid vehicle to be used based on desired viscosity of the adhesive composition.

The binder is preferably an acrylate. More preferably, the binder is an acrylic latex elastomer or plastomer. One example of such a binder is a terpolymer comprising about 60% to about 65% of ethyl acrylate, about 25% to about 30% methyl methacrylate and about 5% to about 10% acrylonitrile (all percentages by weight). It is preferred that the binder is not toxic or offensive to animal and plant life. The binder also must not adversely affect zeolite activity.

Generally, latex polymer are commercially available as aqueous suspensions or dispersions. A surfactant, preferably anionic, is believed to be present in an amount of about 1% to about 3% by weight relative to the binder to help maintain a more uniform latex suspension or dispersion. It is presently preferred that the anionic surfactant is a linear alkyl sulfate, such as sodium lauryl sulfate, for example. One example of a binder component is Latex S-3110, manufactured by American Finish and Chemical Co. in Chelsea, Mass. Latex S-3110 is an aqueous suspension of a binder (about 52% binder solids, by weight) with a surfactant in accordance with the present invention. One skilled in the art will appreciate, however, that other, suitable binders may be used in accordance with the present invention.

The adhesive composition is present in an amount sufficient to securely bind the zeolite to the nonwoven polymer pad 11 without adversely affecting zeolite activity. It has been found that where the amount of zeolite relative to the binder component of the adhesive composition is relatively high, the zeolite is more readily displaced from the pad 10. Where zeolite is displaced from the pad, the surface area of the zeolite within the pad is reduced and the pad is a less efficient adsorbant for ammonia and other chemicals and minerals. In addition, the fine zeolite particles may be displaced into the surrounding environment, which is wasteful, and the zeolite particles are often difficult to retrieve.

Conversely, where the ratio of zeolite to binder is relatively low, zeolite activity is adversely effected. Although the inventors do not wish to be bound by any particular theory, it is believed that where the ratio of zeolite to adhesive is relatively low, the adhesive composition encases the zeolite and hinders or prevents communication between the surface area of the zeolite and the surrounding environment. The relative amounts of zeolite and adhesive composition used to make a slurry which effectively binds the zeolite substantially throughout the pad can readily be determined empirically without undue experimentation, keeping the desirable impregnated pad characteristics in mind.

It is presently preferred that the ratio of the zeolite to the binder solids of the binder component of the adhesive compositive is about 3.0:1 to about 7.0:1 by weight. In one embodiment of the present invention, for example, the ratio of zeolite to binder solids is about 5.1:1 by weight.

It may be desirable in accordance with the present invention to thicken the adhesive composition for ease in manufacturing zeolite-impregnated pads 10, and/or to produce such a pad that permits a predetermined rate of flow of a fluid therethrough. Preferably, the adhesive composition has a viscosity of about 400 to about 700 cps. It is presently preferred that the adhesive composition has a viscosity of about 400 to about 500 cps where it is desired to impregnate a polyester fiber pad 11 having a weight of about 4 oz/yd$^2$, and a viscosity of about 600 to about 700 cps where it is desired to impregnate a polyester fiber pad having a weight of about 9 oz/yd$^2$ to about 12 oz/yd$^2$.

Such thickening properties may be supplied by a polymeric thickener or stabilizer preferably comprising vinyl acetate, ethyl acrylate, methacrylic acid, N-methylol acrylamide and Rhamsam gum (a naturally occurring resin comprising d-glucopyranuronic acid polymer, deoxyl-l-mannopyranose, d-glucopyranose and acetate, and salts thereof) in an amount sufficient to induce a desired viscosity of the adhesive composition. The thickener should not affect zeolite activity. In addition, it is preferred that the thickener is non-toxic and preferably non-offensive to plant and animal life. One example of such a thickener is L-52, manufactured by Alco Chemical Co. in Chattanooga, Tenn., and available in an aqueous suspension (about 30% solids by weight) with a surfactant. One skilled in the art will recognize that other suitable polymeric thickeners known in the art may be used in accordance with the present invention in amounts readily determined based on desired viscosity of the adhesive composition.

It will be understood by one skilled in the art that a polymeric suspension in accordance with the present invention may form a foamy consistency during preparation of the adhesive composition or during impregnation (discussed below) of the polymeric pad 11. Such foaming is generally undesirable because impregnation of a polymeric pad 11 becomes difficult to control. Moreover, such foaming may hinder the preparation of the adhesive composition. Therefore, it may be desirable to have an anti-foaming agent in the adhesive slurry. Preferable anti-foaming agents include ethyl hexanol, organosilicone oils and kerosene. The anti-foaming agent should not affect zeolite activity nor should the anti-foaming agent be toxic or offensive to plant and/or animal life. One example of such an anti-foaming agent is Anitfoam 999 manufactured by Colloids Inc. One skilled in the art will appreciate that other, similar anti-foaming agents may be used in accordance with the present invention. In addition, one skilled in the art may readily determine the amount of anti-foaming agent necessary to reduce foaming during preparation of the adhesive composition and impregnation of the polymer pads 11 using methods and techniques known in the art.

In general, the components of the slurry are present in the following ranges, stated as percentages by weight of the overall slurry: the zeolite is present in an amount of about 26% to about 40%; the water is present in an amount of about 42% to about 63%; the binder is present in an amount of about 9% to about 14%; the thickener is present in an amount of about 2% to about 4%; and the anti-foaming agent, where desired, is present in an amount of less than about 1%. In one presently preferred embodiment of the present invention, the zeolite is present in an amount of about 32.7%; the liquid vehicle in the form of water is present in an amount of about 52.7%; the binder in the form of an acrylic latex dispersion is present in an amount of about 11.6; the thickener in the form of a polymeric acrylate is present in an amount of about 2.5 to about 3.2%; and an anti-foaming agent is present in an amount of about 0.2%.

It is preferred that the zeolite-adhesive slurry is preferred by vigorously mixing the liquid vehicle, zeolite, binder and anti-foaming agent (where desired) until the suspension is generally uniform. Where it is desired to thicken the zeolite-adhesive slurry, a polymeric thickener may be added and mixed into the mixture described above until the desired viscosity is achieved.

The following, non-limiting example illustrates a presently preferred method of preparing the presently preferred zeolite-adhesive slurry 14 in accordance with the present invention.

EXAMPLE 1

In an open cylindrical mixing tank, 250 pounds of water, one pound of Antifoam 999, and 155 pounds of −325 mesh (44 microns) clinoptilolite were mixed and agitated for about 25 minutes until a uniform mixture was obtained. Fifty-five pounds of Latex S-3110 binder were added to this mixture and stirred for approximately 10 minutes. About 13.5 pounds of L-52 polymeric thickener were then added and stirred for approximately 5 minutes.

It is presently preferred that the liquid vehicle, anti-foaming agent and zeolite are mixed together prior to the addition of the binder. Where it is desired to thicken the zeolite-adhesive slurry, the thickener may then be added until the desired viscosity is obtained. Generally, adding the binder in this order allows a uniform mixture to be more easily obtained before increasing the viscosity of the mixture by adding the binder. One skilled in the art will understand, however, that the zeolite-adhesive slurry may be mixed in a different order, such as, for example, all ingredients at once, in accordance with the present invention.

It is preferred in accordance with the present invention that the add-on weight to the pad of the zeolite and adhesive composition is about 100% to about 300%. As used herein, "add-on weight" refers to the amount by weight of zeolite and adhesive composition relative to the weight of the pad 11 without zeolite and adhesive composition. That is, for example, the weight of zeolite and adhesive composition present in the pad 10 of about 100% to about 300% is about one to about three times the weight of the pad 11 without zeolite and adhesive compostion.

The add-on weight of zeolite and binder composition desired is generally based on the desired economic efficiency of the zeolite-impregnated pad 10. For example, a pad 10 having less than about 100% add-on weight of zeolite and adhesive composition is less effective per pad 10 than a pad 10 having a higher add-on weight. Further, a pad 10 having an add-on weight of more than about 300% of zeolite and adhesive composition is more costly to produce than a pad 10 having less than about 300% add-on weight. Moreover, add-on weights above about 300% are generally undesirable because the impregnated pad becomes less porous.

The suitable add-on weight of the zeolite and adhesive composition used in the zeolite-impregnated pad 10 varies depending upon the size, thickness and use of the impregnated pad. The absorbency of the impregnated pad must be balanced with the porosity of the impregnated pad. In some instances, depending upon the environment and fluids passing through the pad, the adsorbency is less important than the porosity. In other instances, the opposite may be true. Thus, for example, the porosity or air permeability of a 9 oz per square yard pad made of nonwoven polyethylene terephthaltate fibers having an add-on weight of 150% of zeolite and adhesive composition may be about 550 to about 600 cubic feet per minute per square foot and an air pressure of 0.5 inch water differential. One skilled in the art could easily adjust the components of the impregnated pad to achieve the desired aDsorbency and porosity without undue experimentation based on the disclosure herein.

In accordance with the present invention, a zeolite-impregnated pad 10 may be produced by providing a permeable, nonwoven polymer pad 11 described above and impregnating the polymer pad with the non-toxic zeolite-adhesive slurry 14 described above. According to one embodiment of the present invention, and illustrated in the schematic diagram of FIG. 4, a permeable, non-woven polymer pad 11, such as a pad containing polyethylene terephtalate fibers and made using a Rando-Webbing machine, is supplied as a continuous web on a wound roller apparatus 16 so that the polymer pad 10 may be unwound while being fed into the zeolite-adhesive slurry 14, which is preferably in a dip tank 18 and kept agitated so that the slurry remains in suspension.

The zeolite-adhesive slurry 14 prepared in accordance with the present invention readily saturates the permeable non-woven polymer pad 11. Generally, it will be understood that the speed with which the pad 11 passes through the dip tank 18 is directly proportional to the period of time the polymer pad 11 is in contact with the zeolite-adhesive slurry 14 and the amount of saturation that may thereby occur. The period of time the polymer pad 11 is in contact with the zeolite-adhesive slurry may be varied depending upon the thickness and weight of the polymer pad 11, the viscosity of the zeolite-adhesive slurry 14 and the desired add-on weight of the zeolite-adhesive slurry 14 in accordance with the present invention.

Once the polymer pad has passed through the slurry 14 contained in the dip tank 18, it may be desirable to pass the zeolite-adhesive slurry-impregnated pad 10 through means for removing some of the zeolite-adhesive slurry, such as a pair of opposing pressure rollers 20, as illustrated in FIG. 4, or a doctor blade apparatus or other, similar apparatus for removing excess liquid from a non-woven permeable pad, to ensure a desired add-on weight of the zeolite-adhesive slurry 14.

Once the pad is impregnated with the zeolite-adhesive slurry, and, where desired, some slurry has been removed, the wet, impregnated pad 10 is fed into a convection heat oven 22 where the pad is dried or cured. Preferably, the convection heat oven 22 is a forced hot air convection oven. The wet, impregnated pad 10 is preferably heated to a temperature of from about 325° to about 375° F. until the pad 10 is dried to a residual moisture content of up to about 4 percent, which generally requires a drying time of about 2 to about 8 minutes. One skilled in the art may readily determine the temperatures and time necessary to dry or cure (generally called dwell time) the zeolite-impregnated pad 10 in accordance with the present invention using methods and techniques known in the art.

It has been found that in accordance with the present invention, it may be desirable to supplement the convection heat oven 22 to more uniformly dry or cure the zeolite-adhesive slurry 14. Supplemental heating may be supplied by infrared heating and radio frequency heating. Such supplemental heating generally reduces dwell time by about 50% to about 75% of the dwell time of convection heat alone.

The impregnated pad 10 may be drawn through the oven 22 on rollers, a porous conveyor belt or other, similar means known in the art. A clip-type tenter frame conveyor system is preferred to prevent shrinkage of the impregnated pad. One skilled in the art will recognize, however, that other, similar conveyor systems may be used in accordance with the present invention.

The dried impregnated pad 10 may then be wound on a receiving core 24, where it may be sealed in, for example, a polyethylene bag to prevent adsorption of gases and vapors (such as ammonia) in the air by the zeolite.

The pad 10 of the present invention may further be processed by cutting the pad 10 into various shapes depending upon the intended use. Examples of such include rectangular or circular filters for air systems, filters for aquariums, or any other desired shape. One skilled in the art may easily determine further processing steps, including shaping, cutting slits 24, and packaging, depending upon the desired use of the zeolite-impregnated pad 10.

The zeolite-impregnated pad 10 according to the present invention may be used to remove ammonia from a fluid by passing the fluid through or in contact with the zeolite-impregnated pad 10. As described in U.S. Pat. No. 4,437,429, zeolite has a high affinity for free ammonia and other compounds and minerals including potassium, calcium, iron, magnesium and copper, among others. In accordance with the present invention, a fluid is preferably passed through a porous filter comprising a zeolite-impregnated pad 10, whereupon ammonia and minerals, such as those described above are removed from the fluid and adsorbed by the zeolite in the zeolite-impregnated pad 10. Examples of fluids suitable for filtering with a zeolite-impregnated pad in accordance with the present invention include gas and liquid and, in particular, air and water. One skilled in the art will appreciate, however, that other ammonia containing and/or mineral containing fluids may be filtered in accordance with the present invention.

The zeolite-impregnated pads 10 according to the present invention may be used to grow plants in situ by placing the zeolite-impregnated pad 10 adjacent to the roots of the plant. One skilled in the art of horticulture will recognize that many plants thrive on nitrogen and minerals, such as those described above, and may utilize the nitrogen contained in ammonia and other compounds. For example, nitrosomonas, a naturally occurring and prevalent bacterium often found in association with plant roots, converts ammonia adsorbed by a zeolite-impregnated pad to nitrite. Nitrobacter, a similarly occurring bacterium, converts nitrite to nitrate. Nitrates are readily adsorbed by plant roots as food, leaving the zeolite surface free to readsorb more ammonia, and so forth. Zeolite-impregnated pads 10 that have adsorbed nitrogen from nitrogenous compounds and minerals are, therefore, a nutrient-rich environment for plants. It has been found that by placing the roots of plants in communication with zeolite-impregnated pads 10 that have adsorbed nitrogen containing compounds (such as ammonia) and minerals, plant growth is surprisingly enhanced.

In one embodiment of the present invention, a zeolite-impregnated pad 10 having nitrogen from ammonia and other nitrogenous compounds adsorbed thereto is placed adjacent to the roots of the plant so that the roots may receive the nitrogen. It is believed that plant roots may receive nitrogen and other minerals that are also adsorbed by zeolite-impregnated pads 10 by diffusion from the pads to the roots. Plant roots should be placed adjacent to zeolite-impregnated pads so that communication is established between the roots and pad sufficient to induce diffusion or other means of receiving nitrogen and minerals from the zeolite-impregnated pads.

FIG. 1 illustrates a preferred embodiment of the method of using a zeolite-impregnated pad 10 for growing plants 26 in situ. It may be desired to cut slits 24 through the zeolite-impregnated pad 10 where it is desired to use the pad for growing and anchoring plants. Such plants 26 may include land plants, aquatic plants and plantsd grown hydroponically. For example, an aquatic plant 26 may be grown in accordance with the present invention by placing the plant 26 through a slit 24 in a zeolite-impregnated pad 10 so that the roots 28 of the plant 26 are freely movable and in communication with the zeolite-impregnated pad 10. By so placing the plant through a slit 24 in a zeolite-impregnated pad 10, the aquatic plant 26 is firmly anchored, resistant to being uprooted by feeding fish and water currents. The pad 10 having plants 26 placed therethrough may then be positioned, for example, in a fish aquarium under gravel where the plants 26 are free to grow, anchored by the pad and nourished by the ammonia and minerals naturally present in such an aquarium which are adsorbed by the zeolite-impregnated pad 10 and converted to useable nitrates by naturally occurring bacteria.

One skilled in the art recognize that the method of growing plants 26 in situ using zeolite-impregnated pads may also be used in earth environments, where the pads may be positioned on top of or below the soil to help to keep the soil around the plants relatively moist and nourish the plants. Examples of such use include reforestation projects and planting seedlings and cuttings. Such pads may also be used in hydroponic environments, where, for example, pads having slits therein, for example, may be used to nurture and anchor seedlings, cuttings and other easily uprooted plants in accordance with the present invention.

Zeolite-impregnated pad 10 having adsorbed nitrogen compounds and minerals may also be used to grow bacteria, including nitrogen fixing bacteria, such as nitrosomonas and nitrobacter discussed above, by providing a nutrient-rich environment, (viz.: a zeolite-impregnated pad 10 having ammonia and other nitrogenous compounds and minerals adsorbed thereby) in which bacteria may grow.

The present invention may be embodied in other specific forms without departing from the spirit or central attributes thereof and, accordingly, reference should be made to the appended claims, rather than to the foregoing specificiation, as indicating the scope of the invention.

We claim:

1. A zeolite-impregnated pad comprising a permeable, nonwoven polymer pad having zeolite bonded substantially throughout the pad by a non-toxic adhesive composition, and adhesive composition being present in an amount sufficient to securely bind the zeolite to the nonwoven polymer pad without adversely affecting zeolite activity.

2. The pad according to claim 1, wherein the combined weight of the zeolite and the adhesive composition present in the pad is about 1 to about 3 times the weight of the pad without zeolite and adhesive composition.

3. The pad according to claim 1, wherein the nonwoven polymer pad comprises a lofty, nonwoven pad of polymeric fibers generally randomly oriented throughout the pad and bonded together at points where the fibers contact each other.

4. The pad according to claim 3, wherein the combined weight of the zeolite and the adhesive composition present in the pad is about 1.5 times the weight of the pad without zeolite and adhesive composition.

5. The pad according to claim 3, wherein the fibers comprise polyethylene terephthalate.

6. The pad according to claim 5, wherein the fibers are about 5 denier to about 25 denier.

7. The pad according to claim 6, wherein the fibers are about 6 denier, 15 denier and 25 denier present in an amount of about 16%, 66% and 16% by weight, respectively.

8. The pad according to claim 6, wherein the pad has a weight of about 2 oz/yd$^2$ to about 13 oz/yd$^2$.

9. The pad according to claim 7, wherein the pad has a weight of about 9 oz/yd$^2$ and is about 0.50 inch thick.

10. The pad according to claim 1, wherein the zeolite is selected from the group consisting of analcime, sodalite, chabazite, natrolite, phillipsite, mordenite and clinoptilolite.

11. The pad according to claim 10, wherein the zeolite is clinoptilolite.

12. The pad according to claim 1, wherein the adhesive composition for the zeolite comprises a liquid vehicle and binder.

13. The pad according to claim 12 wherein the adhesive composition further comprises a thickener.

14. The pad according to claim 13, wherein the adhesive composition further comprises an anti-foaming agent.

15. The pad according to claim 14, wherein the adhesive composition comprises about 63 to about 93% by weight of the liquid vehicle, about 14 to about 21% by weight of the binder, about 3 to about 6% by weight of the thickener and less than about 1% by weight of the anti-foaming agent.

16. The pad according to claim 12, wherein the liquid vehicle comprises water.

17. The pad according to claim 12, wherein the binder is an acrylate.

18. The pad according to claim 12, wherein the binder is a terpolymer of ethyl acrylate, methyl methacrylate and acrylonitrile.

19. The pad according to claim 12, wherein the binder is a dispersion of binder solids in a liquid component and wherein the ratio of zeolite to binder solids is about 3.0:1 to about 7.0:1 by weight.

20. The pad according to claim 19, wherein the ratio of zeolite to binder solids is about 5.1:1 by weight.

21. The pad according to claim 13, wherein the thickener is a polymeric thickener selected from the group consisting of vinyl acetate, ethyl acrylate, methacrylic acid and n-methylol acrylamide and Rhamsam gum.

22. The pad according to claim 1, wherein the zeolite-impregnated pad comprises a pad of nonwoven polyester fibers bonded together where they contact each other, and clinoptilolite bonded to the fibers by a adhesive composition comprising water, a binder comprising a dispersion of binder solids in a liquid component and further comprising a terpolymer of ethyl acrylate methyl methacrylate and acrylonitrile, a thickener comprising a terpolymer of vinyl acetate, ethyl acrylate and methacrylic acid, and an anti-foaming agent, the combined weight of the clinoptilolite and the adhesive composition being about 1.5 to about 2.0 times the weight of the pad without zeolite and adhesive composition, and the ratio of clinoptilolite to the binder solids being about 5.1:1 by weight.

* * * * *